United States Patent [19]

Sampson

[11] 4,436,547

[45] Mar. 13, 1984

[54] PLANT TECHNIQUE

[75] Inventor: Michael J. Sampson, Chichester, England

[73] Assignee: Staart Enterprises Ltd., London, England

[21] Appl. No.: 85,918

[22] PCT Filed: Mar. 22, 1979

[86] PCT No.: PCT/GB79/00050

§ 371 Date: Nov. 28, 1979

§ 102(e) Date: Oct. 27, 1979

[87] PCT Pub. No.: WO79/00838

PCT Pub. Date: Oct. 18, 1979

[51] Int. Cl.$^3$ .................... A01N 43/48; A01N 43/40; A01N 33/02

[52] U.S. Cl. .......................... 71/76; 71/86; 71/88; 71/89; 71/90; 71/92; 71/94; 71/95; 71/96; 71/98; 71/105; 71/113; 71/120; 71/121; 424/216; 424/225; 424/273 B; 424/274; 424/300; 424/316

[58] Field of Search ............ 71/76, 92, 94, 121, 71/DIG. 1, 79, 65

[56] References Cited

U.S. PATENT DOCUMENTS

| | | | |
|---|---|---|---|
| 2,864,681 | 12/1958 | Nickell | 71/94 |
| 3,118,753 | 1/1964 | Shive et al. | 71/89 |
| 3,156,554 | 11/1964 | Tolbert | 71/76 |
| 3,332,959 | 7/1967 | Braunholtz | 71/74 |
| 3,395,009 | 7/1968 | Oettel et al. | 71/76 |
| 3,458,627 | 7/1969 | Daudin et al. | 424/170 |
| 3,920,443 | 11/1975 | Drewe et al. | 71/94 |
| 4,075,005 | 2/1978 | Knowles et al. | 71/94 |
| 4,212,664 | 7/1980 | Takeuchi et al. | 71/94 |

FOREIGN PATENT DOCUMENTS

| | | | |
|---|---|---|---|
| 885992 | 6/1953 | Fed. Rep. of Germany | 71/94 |
| 1433576 | 2/1966 | France | 424/170 |
| 2143806 | 6/1972 | France | 71/76 |
| 2251262 | 11/1974 | France | 71/76 |
| 2255015 | 12/1974 | France | 71/86 |
| 2338649 | 1/1977 | France | 71/92 |
| 679917 | 9/1952 | United Kingdom | 71/115 |
| 955685 | 4/1964 | United Kingdom | 71/113 |
| 1207787 | 10/1970 | United Kingdom | 71/89 |
| 1498004 | 12/1974 | United Kingdom | 71/79 |
| 1424889 | 2/1976 | United Kingdom | 71/76 |
| 424547 | 10/1974 | U.S.S.R. | 71/76 |
| 641949 | 1/1979 | U.S.S.R. | 71/92 |
| 658128 | 4/1979 | U.S.S.R. | 71/76 |

OTHER PUBLICATIONS

Lee et al., (Lee), Chemical Abstracts, 88208p, "Effect of Chemical Spray on Growth and Yield of Wheat," vol. 79, 1973, p. 95.

Suslavicius, Chemical Abstracts, 27040t, "Effect of Some Vitamins and Succini Acid on the Yield of Winter Cereals and Their Quality," vol. 82, 1975, p. 157.

*Primary Examiner*—Glennon H. Hollrah
*Attorney, Agent, or Firm*—Maky, Renner, Otto & Boisselle

[57] ABSTRACT

In accordance with the invention, the effect of certain agricultural chemicals, viz. fungicides, herbicides, insecticides, nematocides and plant-growth regulators, is improved by co-administration of them with one or more of the following additives: carbohydrates, organic acids (particularly fatty acids and acids of the Krebs tricarboxylic acid cycle), vitamins and co-enzymes, purine and pyrimidine nucleosides and nucleotides, naturally occurring fats and oils, certain amino acids and (but not when the agricultural chemical is itself a plant-growth regulator) plant-growth regulators. The invention provides compositions containing one or more of the said agricultural chemicals and one or more of the said additives, and methods of improving the harvest of a given crop by applying to it one or more of the said agricultural chemicals and one or more of the said additives, either simultaneously or within up to about ten days of one another.

8 Claims, No Drawings

PLANT TECHNIQUE

This invention relates to agricultural chemicals, which term is used herein to mean fungicides, herbicides, insecticides, nematocides and plant-growth regulators, and to methods of using them and compositions containing them.

The present invention is concerned with altering the performance of such chemicals. The conventional approach to this involves altering the chemical structure to a greater or lesser degree without altering the class or basic chemical type to which the compound belongs, and/or altering the physico-chemical properties of a formulation containing the chemical, e.g. by the addition of chemicals to facilitate coating of the target organism with the agricultural chemical or to improve the adhesion and rainfastness of the agricultural chemical. The literature (including patents) is full of examples of how the conventional approach may be carried out. In particular, it is known that addition of wetting agents can enhance the effect of many agricultural chemicals.

The invention is based on the discovery that the efficiency of agricultural chemicals can be markedly improved and that such chemicals can in some cases be used in new and different ways by modifying the organism to which the agricultural chemical is applied, such modification being effected by means of a second chemical herein called an additive. The additive acts in either or both of the following ways, viz., it modifies the way in which the organism takes up and/or moves or internally distributes the chemical, and/or it modifies the metabolism of the organism without affecting take-up or distribution of the chemical, thereby achieving the desired action or improvement in action of the agricultural chemical.

The invention provides an agricultural formulation comprising an agricultural chemical as hereinbefore defined together with an additive as hereinafter defined. Such formulations may be in concentrate form, needing addition of, for example, water to make them ready for use. The invention also provides a method of applying an agricultural chemical to a target organism, in which an additive as hereinafter defined is also applied either simultaneously with the agricultural chemical or not more than 15 days (preferably 10 days) before or after. When the application is simultaneous, the agricultural chemical and additive may be supplied in a single formulation or may be mixed in situ in a spray or other chemical-applying apparatus.

The additives used in the formulations and methods of the present invention are defined as belonging to one of the following classes (a) to (h), although two or more such additives in the same or different classes may be used, as may two or more agricultural chemicals:

(a) a carbohydrate source, (e.g. glucose, hydrolysed starch, sucrose, fructose, glycerol, glyceraldehyde, erythrose, ribulose, xylulose and arabinose and their esters and glycosides and metabolic equivalents of carbohydrates), which will normally be applied at 10 to 10,000 g/ha (grams per hectare), to function as
  (1) A source for the production of high energy bonds as in adenosine triose phosphate (ATP) production,
  (2) For the formation of reduced nicotinamide adenine dinucleotide (NADH) and reduced nicotamide adenine dinucleotide phosphate (NADPH) and
  (3) As precursors of amino acids and nucleotides;

(b) an organic acid, particularly one of the Krebs Tricarboxylic Acid Cycle and their metabolic precursors, (including citric, succinic, malic, pyruvic, acetic and fumaric acids), which will normally be applied at similar rates to and used for similar functions as the carbohydrate source;

(c) a vitamin or coenzyme, e.g. thiamine, riboflavin, pyridoxine, pyridoxamine, pryidoxal, nicotinamide, folic acid, or a precursor thereof including nicotinic acid, which will normally be applied at 0.01 to 500 g/ha to stimulate metabolic processes dependent on enzymatic action;

(d) a purine or pyrimidine nucleoside, nucleotide or a metabolic precursor thereof, e.g. adenine, adenosine, thymine, thymidine, cytosine, guanine, guanosine, hypoxanthine, uracil, uridine or inosine, which will normally be applied at 1 to 500 g/ha to act as structural precursors for nucleic acid synthesis;

(e) a fatty acid of a type found in natural saturated and unsaturated fats, e.g. butyric, lauric, palmitic, stearic, oleic and linoleic acid, which will normally be applied at 10 to 10,000 g/ha to act as precursors of molecules required in growth process and through their degradation to provide a source of ATP and NADPH as with a carbohydrate source;

(f) a naturally occurring fat or oil including olive, soya, coconut and corn oils, which can be degraded by living organisms to fatty acids and which will normally be applied at 10 to 10,000 g/ha;

(g) an amino acid of a type that occurs naturally in plant proteins, e.g. glycine, alanine, valine, leucine, isoleucine, serine, threonine, cysteine, methionine, aspartic acid, glutamic acid, glutamine, asparagine, lysine, hydroxylysine, arginine, histidine, phenylaline, tyrosine, tryptophan, proline or hydroxyproline, which will normally be applied at 1 to 500 g/ha to act as structural units for newly formed proteins or by their degradation to function in a similar manner to fatty acids and carbohydrates;

(h) a naturally occurring plant-growth regulator (provided that the agricultural chemical itself is not a plant-growth regulator) of the type that affects the basic metabolic processes of a plant so as to render an applied pesticide more effective, e.g. indole-3-acetic acid and gibberellic acid, which are normally used in amount such that the final concentration in a spray applied to the crop is 0.5 to 1000 parts per million by weight.

The additives in groups (a) to (g) above are especially effective in enhancing the plant-growth-regulating effect of quaternary ammonium compounds of the formula $R-N(CH_3)_3-Y$ in which Y is a non-phytotoxic anion and R is a lower aliphatic radical (e.g. a $C_{1-8}$ or $C_{1-6}$ aliphatic radical) containing a non-ionizing nucleophilic group or atom, e.g. haloalkyl, alkylene, haloalkylene, cyanoalkyl, mercaptoalkyl, alkoxyalkyl, alkylthioalkyl or epithioalkyl. Such compounds are defined in more detail in U.S. Pat. No. 3,156,554 and a specific example of such a compound is chlorocholine chloride, which has the systematic chemical name β-chloroethyl trimethylamonium chloride. It is also known as chlormequat or CCC. The known action of such compounds when applied as a foliar spray includes the ability to shorten and strengthen the stems of wheat, oats and rye, though not of barley or rice. Such a shortening and strengthening is sometimes, though not consistently, accompanied by the formation of a better developed root system and the survival of a higher proportion of the tillers or side shoots. While such effects on roots and tillers where they occur may be beneficial in themselves, the principle use of a chlormequat or similar treatment has been to prevent the 'lodging' or collapsing of the cereal plant as the result of strong winds. Such lodging being known to result in loss of yield and difficulty in harvesting.

The use of compositions in accordance with the present invention can enhance the effectiveness of chlormequat, especially under poor growing conditions, for example, where the temperature for some days after application of the growth regulator does not exceed 10° C. This condition is commonly encountered during the time at which a cereal plant is reaching the end of the growth stage in which tillers are produced (Growth Stage 4–5). It is frequently desirable to apply the growth regulator at this stage, because certain fungicides and herbicides are also desirably applied before Growth Stage 6, and because crop damage is more likely to occur when the plant has been treated during Growth Stage 6 (at which stage the first 'node' or joint has formed on the tiller) and then encounters a check to growth, as for instance the result of drought.

The normal range of application times is from Growth Stage 4–Growth Stage 6, all of which occur early in the year when the temperatures may be low.

In addition to improving on the known action of chlormequat on stem, roots and tiller survival in wheat, oats and rye, compositions of the present invention may also be used to obtain an action on other cereal plants where chlormequat on its own has failed to give a useful result, as for instance with barley and rice, and to reduce the application rate of chlormequat.

Such additives may also be beneficially used with other cereal-growth regulators to obtain effects similar to those obtained by their use in conjunction with chlormequat. Such cereal-growth regulators include, but are not limited to, the following growth regulators used singly or in combination, including combinations with the quaternary ammonium growth regulators described above:

1. Haloalkyl phosphoric acids (particulary β-haloalkylphosphoric acids and especially acids in which the halogen is chlorine) and compounds of the general formula

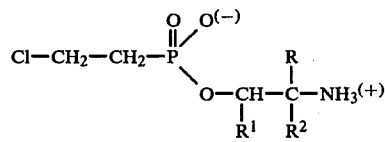

where each of R, R¹ and R², which are identical or different, is a hydrogen atom or a $C_{1-3}$ alkyl radical. Examples of non-phytotoxic anions are chloride, bromide, methosulphate, sulphate and phosphate. A particularly useful example is 2-chloroethyl phosphoric acid. (CEPA). Such compounds are defined in detail in U.K. Pat. No. 1,483,915.

2. Chlorphonium chloride, i.e. tributyl-2,4-dichlorobenzyl-phosphonium chloride.

3. Mepiquat chloride.

4. A diphenyl-1H-pyrazolium salt of the formula

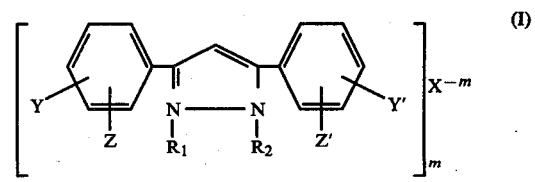

where $R_1$ is methyl; $R_2$ is alkyl $C_1$–$C_4$; X is an anion with a charge of 1 to 3; Y, Y', Z and Z' are hydrogen, halogen, methyl or methoxy; and m is an integer from 1 to 3; provided that only one phenyl ring can be substituted on the carbon para to the pyrazolium ring with a substituent other than hydrogen. These compounds are defined in detail in U.K. Pat. No. 1,466,634. Such compounds also act as specific herbicides selectively controlling wild oats in wheat and barley crops. The said additives may also be used to enhance this herbicidal action.

HERBICIDES (Substances for killing and/or controlling unwanted plants)

A number of herbicides check the growth of weeds so rapidly that the target plant has its metabolism so reduced that the herbicide does not completely kill it. Thus, after an interval during which the herbicide is degraded or suffers a change of form or is removed from those sites where its lethal action is exerted, the weed may then re-commence growth. A particular problem in agriculture is the control of wild oats, where a number of commonly used herbicides show such an effect, especially where the wild oat has become a well established plant. By stimulating growth and uptake of applied chemicals it is possible to enhance the activity of a number of herbicides, especially against older more established weeds.

Herbicides that may benefit from applications in conjunction with those substances comprising the subject of this patent include, but are not limited to, those herbicides listed below. The names used are those trivial names used in the "Pesticide Index":

1. Barban
2. Benzoyl-propethyl
3. Chlorfenprop-methyl
4. Chlortoluron
5. Difenzoquat
6. Diclofop-methyl
7. Flamprop-ispropyl
8. Flamprop methyl
9. Isoproturon
10. Atrazine
11. Simazine
12. Linuron
13. Trifluralin
14. Hormone type weedkillers including MCPA, 2,4-D, MCPB, 2,4-DB, Mecoprop, Dichlorprop, Ioxynil, Bromoxynil, Benazolin, Bentazone, Cyanazine, Dicamba, Dinoseb-amine, Dinoseb-acetate
15. Dalapon
16. Phenmedipham
17. Glyphosate
18. Asulam
19. Nitrofen
20. Desmetryme
21. Propachlor
22. Propyzamide
23. Diallate 24. Triallate A further aspect of this invention is the use of the substances forming this invention to enable a herbicide to be sprayed later than would otherwise have been possible. This is important since:
(a) A period of weather unfavourable to spraying may allow weeds to grow beyond the stage or size at which they may be satisfactorily controlled.
(b) By making it possible to treat older weeds a longer period is allowed for other weeds to germinate and become susceptible to the action of a foliar (leaf-applied) herbicide.
(c) By enabling spraying to take place later, it may enable the crop to become better established and less at risk to damage from the applied agricultural chemical.

A particular example of the use of such substances to enable spraying to be delayed is their use in conjunction with chlortoluron, CN-(3-chloro-4-methylphenyl)-N,N-dimethyl urea, such that it will control wild oats (Avenna spp) that have passed the two-leaf stage (ZCK 12) and blackgrass (Alopecurus spp) that has passed the five-leaf stage (ZCK 15). Known formulations will give only a poor control of wild oats up to the two-leaf stage and negligible control thereafter. Blackgrass will be controlled satisfactorily only up to the five-leaf stage. Since blackgrass and wild oats germinate over an extended period it is possible to have late-germinating weeds emerging while early-germinating weeds have passed the stage at which they may be controlled. For this reason chlortoluron is used primarily as a soil-applied chemical acting through the weed roots. By extending the period at which emerged weeds may be controlled a useful alternative method of application independent of soil conditions is provided. In the autumn conditions may be unsuitable for soil application either because of excessive water or excessive dryness.

A specific aspect of this invention involves the enhancement of the herbicidal activity of bipyridylium herbicides. The metabolism of a target weed organism may be modified in a specific manner by modifying a distinctive biochemical pathway or reaction in order to enhance the activity of an agricultural chemical.

The lethal action of the bipyridyl herbicides paraquat (1,1¹-dimethyl-4,4¹ dipyridylium salt) and diquat (1,1¹-ethylene-2,2¹ dipyridylium) is the result of the formation of hydrogen peroxide when the paraquat or diquat ion, having been reduced to the free radical by the photosynthetic electron flow, is re-oxidized by molecular oxygen, thus re-forming the paraquat or diquat ion and H₂O₂. As this can happen very rapidly (especially in bright sunshine) it is possible for the herbicide to destroy superficial leaf cells where droplets of herbicide solution have fallen and thus prevent its own continued uptake into the bulk of the plant cells.

The speed of the lethal action may be slowed down by providing an alternative oxidation/reduction system. Thus the use of oxidized glutathione (GSSG) in conjunction with a bipyridyl herbicide can be used to re-oxidize the reduced free radical while forming reduced glutathione (GSH). If this system is coupled with another system or systems to re-oxidize the reduced glutathione then the glutathione will act in more than a simple stoichiometric relationship with the herbicide.

One such system is the enzymic re-oxidation of reduced glutathione in conjunction with nicotine adenine dinucleotide phosphate (NADP), which may be stimulated by the use of an NADP precursor such as nicotinamide or nicotinic acid, and a further system is that of ascorbic acid/dehydroascorbic acid catalysed by the enzyme ascorbic acid oxidase, which may be stimulated by the use of ascorbic acid. Ascorbic acid is initially added and converted in the plant to dehydroascorbic acid-(5) below. The reactions that take place with paraquat and GSSG are thus:

$$\text{Paraquat ion} \xrightarrow{\text{light}} \text{reduced free radical} + \tfrac{1}{2}O_2 \quad (1)$$

$$\text{reduced free radical} + O_2 + H_2O \longrightarrow \text{Paraquat ion} + H_2O_2 \quad (2)$$

$$\text{reduced free radical} + GSSG \longrightarrow \text{Paraquat ion} + GSH \quad (3)$$

$$GSG + \text{dehydroascorbic acid} \longrightarrow \text{ascorbic acid} + GSSG \quad (4)$$

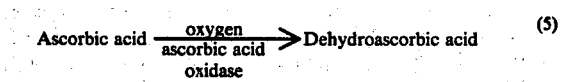

$$\text{Ascorbic acid} \xrightarrow[\text{ascorbic acid oxidase}]{\text{oxygen}} \text{Dehydroascorbic acid} \quad (5)$$

Thus some of the free radical from the paraquat is temporarily mopped up, and the formation of H₂O₂ effectively slowed down while re-forming the paraquat ion.

FUNGICIDES AND INSECTICIDES (i.e. substances for killing and/or controlling fungi and insects)

The beneficial activity of these materials can be enhanced in accordance with the invention. Thus by stimulating the metabolism the fungus is less able to resist the toxic effects of the chemical by having its growth temporarily restricted while a systemic fungicide or insecticide which must penetrate through the plant for maximum effect may more readily do so.

The insecticides and fungicides where effects be beneficially modified in accordance with the invention include, but are not limited to, the following:

| Fungicides | |
|---|---|
| Captan | Mancozeb |
| Captafol | Vinclozin |
| Dimethirimol | Zineb |
| Benodanil | Thiram |
| Maneb | Chloropyriphos |
| Tridemorph | Triazophos |
| Triadimephon | Binapacryl |
| Thiabendazole | Bupirimate |
| Triforine | Ditalimfos |
| Carbendazim | Sulphur |
| Dodine | |
| Thiophanate methyl | |
| Pyrazophos | |
| Ethirimol | |

| Insecticides | | |
|---|---|---|
| Demeton-S—methyl | Pirimiphos-methyl | Lindane |
| Pyrimicarb | DDT | Fonofos |
| Vamidothion | Azinphozmethyl | DNOC |
| Demephion | Trichlorphon | |
| Menazon | Triazophos | |
| Dimethoate | Malathion | |
| Dimefox | Phosalone | |
| Fenitrothion | Carbaryl | |

-continued

| Phosphamidon |
|---|

In a further aspect of this invention, the activity of an agricultural chemical not containing an additive as hereinbefore described as a metabolic stimulant will have its own activity stimulated or otherwise beneficially modified as the result of being applied in conjunction with an agricultural chemical formulated with such a substance.

The toxicity of compositions in accordance with the present invention may be reduced by including in the mixture a compound that acts as a purgative or emetic or that acts to delay uptake of the material in the alimentary canal. Suitable purgatives include phenolphthalein, senna extract and castor oil. Apomorphine is a useful emetic, whose effect is enhanced by the presence of ethyl alcohol. The amount of emetic that is added (e.g. to paraquat) is such that if sufficient agricultrual chemical is ingested to cause a toxic response, sufficient emetic is ingested to cause emesis.

References in the specification to growth stages in weeds are those defined in the "Weed Control Handbook", ed J D Fryer and R L Makepeace, Blackwell Scientific Publications, e.g. in the 6th Edition.

The following are illustrative Examples of compositions in accordance with the invention. 225 liters of spray solution is normally used per hectare.

| Example | | Additives per 225 liters of spray solution |
|---|---|---|
| I | Glycerol | 75 ml. |
|  | Alkyl phenol ethylene oxide condensate (wetting agent) | 175 ml. |
|  | Nicotinamide | 3 g. |
|  | Pyridoxine | 1.5 g. |
|  | Yeast extract | 3 g. |
| II | Glucose syrup | 500 g. |
|  | Triton - X 100 (wetting agent) | 250 ml. |
|  | Yeast extract | 80 g. |
| III | Glycerol | 100 ml. |
|  | Alkyl phenol ethylene oxide condensate (wetting agent) | 300 ml. |
|  | Citric acid | 100 g. |
|  | Sucrose | 150 g. |
| IV | Glycerol | 300 ml. |
|  | Gibberellic acid | 50 g. |
|  | Alkyl phenoleethylene oxide condensate (wetting agent) | 200 ml. |
| V | Yeast extract | 200 g. |
|  | Asparagine | 20 g. |
|  | Methionine | 15 g. |
|  | Cysteine | 15 g. |
| VI | Ascorbic acid | 60 g. |
|  | Nicotinamide | 10 g. |
|  | Glycerol | 100 ml. |
|  | Glutathione | 25 g. |
|  | Alkyl phenol ethylene oxide condensate (wetting agent) | 200 ml. |
| VII | Corn oil | 1000 ml. |
|  | Nicotinamide | 5 g. |
|  | Pyridoxine | 5 g. |
|  | Yeast extract | 10 g. |
|  | Glycerol | 75 ml. |
| VIII | Corn oil | 750 ml. |
|  | Gibberellic acid | 5 g. |
|  | Glucose syrup | 250 g. |
| IX | Olive oil | 500 ml. |
|  | Alkyl phenol ethylene oxide condensate (wetting agent) | 500 ml. |
|  | Sucrose | 200 g. |
|  | Yeast extract | 10 g. |
| X | Corn oil | 250 ml. |

-continued

| Example | | Additives per 225 liters of spray solution |
|---|---|---|
|  | Nicotinamide | 5 g. |
|  | Yeast extract | 30 g. |
|  | Methionine | 5 g. |
|  | Glycerol | 60 ml. |
|  | Alkyl phenol ethylene oxide condensate (wetting agent) | 200 ml. |
| XI | Corn oil | 1000 ml. |
|  | Chlorocholine chloride | 800 g. |
|  | Nicotinamide | 5 g. |
|  | Pyridoxine | 5 g. |
|  | Yeast extract | 10 g. |
|  | Glycerol | 75 ml. |
| XII | Sucrose | 100 g. |
|  | Yeast extract | 5 g. |
|  | Citric acid | 25 g. |
|  | Asparagine | 10 g. |
|  | Alkyl phenol ethylene oxide condensate (wetting agent) | 50 ml. |
| XIII | Ascorbic acid | 50 ml. |
|  | Ascorbic acid | 60 g. |
|  | Nicotinamide | 10 g. |
|  | Glycerol | 100 ml. |
|  | Glutathione | 25 g. |
|  | Alkyl phenol ethylene oxide condensate (wetting agent) | 200 ml. |
|  | Ethyl alcohol | 60 ml. |

The following experimental data show effects produced by certain compositions and methods in accordance with the present invention and compare such effects with those of the prior art. In this connection, it should be noted that the further addition of a wetting agent to a standard commercially obtainable formulation of a pesticide is known in some cases to improve its efficacy. Therefore in comparative trials a wetting agent corresponding to that in the combination of additives was also used with the application of the standard formulation.

In comparing the quantities of materials used, it is to be understood that where amounts of agricultural chemical, additive or wetting agent are given per hectare, this means amounts per 225 liters of solution, always expressed in terms of the active ingredient.

In Experiments 1 to 4, the "Standard" is a Standard commercially obtainable formulation with additional wetting agent of the type and in the amount shown in Example I, and the "Standard+Additive" is the same Standard formulation with additives as shown in Example I.

EXPERIMENT 1

Low Temperature—Wheat

This is a comparison of a standard commercially available formulation of Chlormequat, viz. Mandops Chlormequat 46, with the same formulation to which additives as in Example I have been added, with respect to their abilities to shorten the stems of wheat when the temperature does not rise above 7° C. for 5 days before and for 5 days after application. Results are expressed as an average of 250 measurements.

|  | Stem Height cm | % Reduction |
|---|---|---|
| Control (untreated) | 96.4 | — |
| Standard | 88.3 | 8.4 |
| Standard + Additives | 83.9 | 13.0 |

The application rate is equivalent to 7.16 g. of Chlormequat per liter sprayed to run-off on pot-grown plants of Maris Huntsman at Growth Stage 5. The plants were maintained for 5 days before and after spraying at below 7° C., and were then moved to field conditions.

EXPERIMENTS 2(a) AND 2(b)

Barley

This is the effect on stem height in (a) spring barley and (b) winter barley of 1.6 kg per hectare of chlormequat+additive as in Example I. Application is made at Growth Stage 6 (1st "Node" Stage) in 225 liters per hectare of water. Results are expressed as average of 250 measurements.

|  | Stem Height cm | % Reduction |
|---|---|---|
| (a) Spring barley (Mazurka) | | |
| Control (untreated) | 87.4 | — |
| Standard | 86.2 | 1.4 |
| Standard + Additives | 76.3 | 12.7 |
| (b) Winter barley (Igri) | | |
| Control (untreated) | 91.2 | — |
| Standard | 90.2 | 1.1 |
| Standard + Additives | 80.9 | 11.3 |

EXPERIMENT 3

Rice

A standard commercially available formulation of chlormequat is compared with the same formulation to which additives (as in Example I) have been added.

|  | % Reduction in stem height |
|---|---|
| Control (untreated) | — |
| Standard | 1.1 |
| Standard + Additives | 11.3 |

Rate of application is equivalent to 7.1 g. of Chlormequat per liter sprayed to run-off onto plants 20 cm in height.

EXPERIMENTS 4(a) AND 4(b)

Wheat

A standard commercially available formulation of chlormequat is compared with the same formulation to which additives (as in Example I) have been added, with respect to their abilities to shorten the stems of wheat (var. Maris Huntsman).

|  | Average of 250 measurements | |
|---|---|---|
|  | Stem Height cm | % Reduction |
| (a) Control | 94.2 | — |
| Standard | 83.6 | 11.3 |
| Standard + Additives | 80.4 | 14.6 |
| (b) Standard | 82.3 | 12.6 |
| Standard + Additives | 79.8 | 15.3 |

Rate of application is equivalent to 1.2 kg of chlormequat per hectare (Standard (a)) and to 1.6 kg per hectare (Standard (b)) applied in 225 liters per hectare at Growth Stage 6 (1st "Node" Stage).

EXPERIMENTS 5(a) AND 5(b)

Effect of Chlortoluron on Wild Oats

This is a comparison of a commerically available formulation of chlortoluron, viz. that sold under the trade mark "Dicurane", with the same formulation to which additives as in Examples VII and XI have been added with respect to their abilities to control wild oats.

The application rate is equivalent to 3.6 kg Chlortoluron per hectare in 225 liters of water.

(a) Wild Oats sprayed at 5-leaf unfolded Stage (ZCK 15)

|  | % kill of wild oats |
|---|---|
| Standard formulation with additional wetting agent of the type and in the amount shown in Example VII | 15 |
| Standard formulation with additives as shown in Example VII | 62 |
| Standard formulation with additives as shown in Example XI | 80 |

(b) Wild Oats sprayed at 7-leaf unfolded stage

|  | % kill of wild oats |
|---|---|
| Standard formulation with additional wetting agent of the type and in the amount shown in Example VII | 5 |
| Standard formulation with additives as shown in Example VII | 48 |
| Standard formulation with additives as shown in Example XI | 71 |

EXPERIMENTS 6(a) AND 6(b)

Effect of Paraquat

A standard commercially available formulation of paraquat, viz. Gramoxone, is compared with the same formulation to which additives as in Example VI have been added with respect to (a) to their abilities to destroy an old grass sward and (b) to kill a population of mixed and broad leaf and grass seedling weeds at from 2–5 leaf stage. In this experiment the "Standard" is a Gramoxone with additional wetting agent of the same type and in the same quantity as in Example VI and the "Standard+Additives" is Gramoxone+Additives as shown in Example VI.

(a) The application rate is equivalent to 1.1 kg of paraquat per hectare in 400 liters of water. The kill of sward is assessed 4, 8 and 12 days after application.

|  |  | Score (0 = nil effect, 10 = 100% kill) | | |
|---|---|---|---|---|
|  |  | 4 days | 8 days | 12 days |
| Trial 1. | Standard | 4 | 6 | 7 |
|  | Standard + Additives | 2 | 4 | 9 |
| Trial 2. | Standard | 2 | 5 | 6 |
|  | Standard + Additives | 1 | 3 | 8 |

(b) Application rate is equivalent to 0.25 kg of paraquat per hectare in 200 liters of water. Control assessed at 2, 6 and 10 days after application.

|  | % Control | | |
|---|---|---|---|
|  | 2 days | 6 days | 10 days |
| Standard | 5 | 6 | 6 |
| Standard + Additives | 3 | 7 | 8 |

EXPERIMENT 7

Glyphosate

A standard commercially available formulation, viz. that sold under the trade mark "Roundup", is compared with the same formulation to which additives as in Example XII have been added. A mixed week population (grasses and broad leaf weeds) was sprayed and assessed after 2 weeks (0=nil effect, 10=complete kill).

|  | Weed control |
|---|---|
| Roundup (0.7 Kg/ha glyphosate) with wetting agent of the type and in the amount shown in Example XII | 7 |
| Roundup (0.7 Kg/ha glyphosate) with additives as shown in Example XII | 7 |
| Roundup (0.5 Kg/ha glyphosate) with additives as shown in Example XI | 9 |

EXPERIMENT 8

Fungicides

Standard commercialy available formulations of (a) captan (b) thiophanate-methyl and (c) dodine were compared with the same formulations to which additives as in Example X have been added, with respect to their abilities to control black spot of roses.

| (a) Captan | % Control (14 days after spraying) |
|---|---|
| Standard (Mandops Captan 83) | 78 |
| Standard + Additives | 95 |

The rate of application is equivalent to 100 grams of captan per 100 liters of water sprayed to run-off.

| (b) Thiophanate-methyl. | % Control (14 days after spraying) |
|---|---|
| Standard (Benlate) | 72 |
| Standard + Additives | 90 |

Rate of application is equivalent to 46 g. of thiophanate per 100 liters of water sprayed to run-off.

| (c) Dodine | % Control (14 days after spraying) |
|---|---|
| Standard (Mandops dodine 65) | 84 |
| Standard + Additives | 96 |

The rate of application is equivalent to 60 g. of Dodine per 100 liters of water sprayed to run-off.

In this Experiment, the "Standard" is the indicated standard commercially obtainable formulation with additional wetting agent of the type and in the quantity used in Example X and the "Standard+Additives" is a standard commercially obtainable formulation with additives as shown in Example X The word "Benlate" is a trade mark.

EXPERIMENT 9

Effect of carbendazim on eyespot of wheat

A standard commercially available formulation of carbendazim, viz. that sold under the trade mark Bavistin, is compared with the same formulation to which additives as in Example X have been added with respect to their abilities to control eyespot disease of wheat (var Maris Huntsman).

|  | % Control of Eyespot leaf Infestation in July |
|---|---|
| (a) Bavistin together with additional wetting agent of the same type and in the same quantity as used in Example X | 64 |
| Bavistin with additives as shown in Example X | 75 |
| (b) Bavistin together with additional wetting agent of the same type and in the same quantity as used in Example X | 76 |
| Bavistin with additives as shown in Example X | 90 |

Application rate is equivalent to 250 grams of carbendazim per hectare in Standard (a) and 500 grams of carbendazim per hectare in Standard (b). Application was made at Growth Stage 5.

EXPERIMENT 10

Insecticides

Comparison of a standard commercially available formulation
(a) demeton-S-methyl, viz. Mandops Demeton-S-Methyl 50, and
(b) Dimethoate, viz. Mandops Dimethoate 40
with the same formulation to which additives as in Example IX have been added, with respect to their aphicidal action on potatoes.

|  | % control of aphids 24 hours after spraying |
|---|---|
| (a) Mandops Demeton-S—methyl 50 with additional wetting agent of the same type and quantity as in Example IX | 82 |
| Mandops Demeton-S—methyl 50 with an additive as shown in Example IX | 95 |
| (b) Mandops Dimethoate 40 with additional wetting agent of the same type and quantity as in Example IX | 75 |
| Mandops Dimethoate 40 with additives as shown in Example IX | 88 |

The rates of application were, for demeton-S-methyl, 22 gms/100 liters of water and for dimethoate, 33.6 gms/100 liters of water.

EXPERIMENT 11

Toxicity Studies on chlormequat

The additives used in accordance with the present invention can have an effect on the toxicity of chlormequat even without the addition of purgatives or emetics. For example, in young adult rats the $LD_{50}$ of aqueous chlormequat corresponding to the formulation used in Experiments 1 to 4 is 600 mg/kg, but it becomes 820 mg/kg by the addition of 47 ml of glycerol and 109 ml of alkylphenol ethylene oxide condensate per 1 kg of chlormequat.

I claim:

1. A method of applying an agricultural chemical comprising the steps of
   (A) applying an effective amount of an agricutural chemical to a locus to regulate the growth of plants, said agricultural chemical being selected from the group consisting of
   quaternary ammonium compounds of the formula $R-N(CH_3)_3-Y$ in which Y is a non-phytotoxic anion and R is an aliphatic radical of from 1 to 8 carbon atoms containing a non-ionizing nucleophilic group or atom; and
   (B) applying an effective amount of additive to modify the metabolism of plants to the same locus as said agricultural chemical not more than 15 days earlier than or more than 15 days later than the application of said agricultural chemical, said additive being vitamins or coenzymes selected from the group consisting of thiamine, riboflavin, pyridoxine, pyridoxamine, pyridoxal, nicotinamide, folic acid, or the precursors of said vitamins or coenzymes.

2. A method as claimed in claim 1 in which said agricultural chemical is chlorocholine chloride and it is applied to wheat, oats or rye.

3. A method as claimed in claim 1 in which said agricultural chemical is chlorocholine chloride and it is applied to rice or barley.

4. A method as claimed in claims 2, 3, or 1 in which the agricultural chemical and the additive are applied by spraying onto plants.

5. A method as claimed in any of claims 1, 3, or 4 wherein steps (A) and (B) are performed together, and including step (C)
   (C) applyiing an additional amount of the agricultural chemical used in step (A) to said locus not more than 15 days before and not more than 15 days after steps (A) and (B).

6. A composition for regulating the growth of plants comprising
   (A) an agricultural chemical selected from the growth consisting of
   quaternary ammonium compounds of the formula $R-N(CH_3)_3-Y$ in which Y is a non-phytotoxic anion and R is an aliphatic radical of from 1 to 8 carbon atoms containing a non-ionizing nucleophilic group or atom; and
   (B) an additive, said additive being vitamins or coenzymes selected from the group consisting of thiamine, riboflavin, pyridoxine, pyridoxamine, pyridoxal, nicotinamide, folic acid, or the precursors of said vitamins or coenzymes, component (B) being provided in an effective amount to stimulate the metabolic process of said plants to enhance the growth-regulating effect of component (A).

7. A composition as claimed in claim 6 in which the agricultural chemical is chlorocholine chloride.

8. A composition as claimed in claims 7 or 6 in the form of a sprayable liquid.

* * * * *

UNITED STATES PATENT AND TRADEMARK OFFICE
CERTIFICATE OF CORRECTION

PATENT NO. : 4,436,547
DATED : March 13, 1984
INVENTOR(S) : Michael J. Sampson

It is certified that error appears in the above-identified patent and that said Letters Patent is hereby corrected as shown below:

Title Page, Assignee:, delete "Staart Enterprises Ltd., London, England".

Signed and Sealed this

Fifteenth Day of November, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 4,436,547
DATED : March 13, 1984
INVENTOR(S) : Michael J. Sampson

It is certified that error appears in the above-indentified patent and that said Letters Patent is hereby corrected as shown below:

Title page, Assignee;, delete "Staart Enterprises Ltd., London, England.

Signed and Sealed this

Twenty-first Day of March, 1995

Attest:

BRUCE LEHMAN

*Attesting Officer*          *Commissioner of Patents and Trademarks*